United States Patent [19]

Kiefer et al.

[11] Patent Number: 5,189,216
[45] Date of Patent: Feb. 23, 1993

[54] ISOLATION OF A CARBOXYLIC ACID FROM AN AQUEOUS SOLUTION THEREOF

[75] Inventors: Hans Kiefer, Wachenheim; Werner Reutemann, Bobenheim-Roxheim, both of Fed. Rep. of Germany

[73] Assignee: BASF Aktiengesellschaft, Ludwigshafen, Fed. Rep. of Germany

[21] Appl. No.: 730,768

[22] Filed: Jul. 16, 1991

[51] Int. Cl.$^5$ .............................................. C07C 51/42
[52] U.S. Cl. .................................. 562/600; 562/608; 562/609
[58] Field of Search .......................... 562/600, 608, 609

[56] References Cited

U.S. PATENT DOCUMENTS

| | | | |
|---|---|---|---|
| 2,568,095 | 9/1951 | Smith et al. | 260/450 |
| 4,217,460 | 8/1980 | Hohenschutz et al. | 562/609 |
| 4,551,208 | 11/1985 | Bott et al. | 203/60 |

FOREIGN PATENT DOCUMENTS

| | | |
|---|---|---|
| 0071293 | 2/1983 | European Pat. Off. |
| 2545658 | 4/1977 | Fed. Rep. of Germany |
| 3428319 | 2/1986 | Fed. Rep. of Germany |

*Primary Examiner*—José G. Dees
*Assistant Examiner*—Porfirio Nazario
*Attorney, Agent, or Firm*—Keil & Weinkauf

[57] ABSTRACT

A process for the isolation of a carboxylic acid of the general formula (I)

$$R^1-COOH \qquad (I),$$

in which $R^1$ denotes hydrogen, methyl, ethyl, or vinyl, from a dilute aqueous solution thereof by extraction with a secondary amide of the general formula (II)

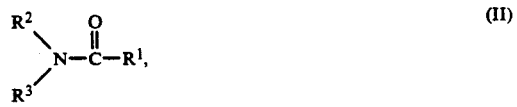

in which $R^1$ has the meanings stated, and $R^2$ and $R^3$ are independently of each other $C_1$-$C_8$-alkyl, $C_3$-$C_8$-cycloalkyl, $C_4$-$C_{20}$-cycloalkylalkyl, aryl, $C_7$-$C_{20}$-aralkyl, or $R^2$ and $R^3$ together form a 1,4- or 1,5-alkylene group which may be mono- to penta-substituted by $C_1$-$C_4$-alkyl, wherein the losses of secondary amide (II) are compensated by the addition of the corresponding amine of the general formula (III)

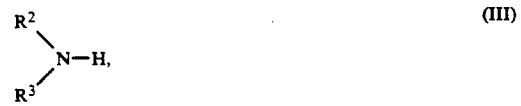

in which $R^2$ and $R^3$ have the meanings stated above.

1 Claim, No Drawings

ISOLATION OF A CARBOXYLIC ACID FROM AN AQUEOUS SOLUTION THEREOF

The present invention relates to a novel and improved process for isolating a carboxylic acid from an aqueous solution thereof using a secondary amide, wherein the losses of secondary amide are compensated by the addition of the corresponding amine.

DE-A 2,545,658 describes a method of isolating a carboxylic acid from an aqueous solution thereof using a secondary amine, but losses of secondary amide incurred during extraction have to be compensated for by the addition of appropriate amounts of secondary amide.

It is thus an object of the invention to overcome this drawback.

Accordingly, we have found a novel and improved process for the isolation of a carboxylic acid of the general formula (I)

$$R^1\text{—COOH} \qquad (I),$$

in which $R^1$ denotes hydrogen, methyl, ethyl, or vinyl, from a dilute aqueous solution thereof by extraction with a secondary amide of the general formula (II)

in which $R^1$ has the meanings stated, and $R^2$ and $R^3$ are independently of each other $C_1$–$C_8$-alkyl, $C_3$–$C_8$-cycloalkyl, $C_4$–$C_{20}$-cycloalkylalkyl, aryl, $C_7$–$C_{20}$-aralkyl, or $R^2$ and $R^3$ together form a 1,4- or 1,5-alkylene group which may be mono- to penta-substituted by $C_1$–$C_4$-alkyl, wherein the losses of secondary amide (II) are compensated by the addition of the corresponding amine of the general formula (III)

in which $R^2$ and $R^3$ have the meanings stated above.

Since transamidation can occur with the carboxylic acid (I), the secondary amides (II) used as extracting agents are such that the radical $R^1$ therein is the same in compounds (I) and (II). Thus it is convenient to extract formic acid with a formamide, acetic acid with an acetamide, propionic acid with a propionamide, and acrylic acid with an acrylamide, so that no outward signs of transamidation are detectable. If mixtures of different acids, for example formic and acetic acids, are to be isolated, it is preferred to use compounds of the formamide series, these being the most effective representatives of the above-defined class of compounds.

With regard to the amide groups, particularly suitable compounds (II) or mixtures thereof are those which are derived from the secondary amines (III), examples of which are N-ethyl-n-cyclohexylamine, N,N-dicyclohexylamine, N-methyl-N-benzylamine, N-methylaniline, N-ethylaniline, N,N-diamylamine, N-methyl-N-2-ethylhexylamine, N-n-butyl-N-cyclohexylamine, N-methyl-N-2-heptylamine, and N-propyl-N-cyclohexylamine. The most suitable extracting agents are the dibutylformamides, particularly di-n-butylformamide, for formic acid, and N-n-butyl-N-2-ethylhexylacetamide or N-n-butyl-N-cyclohexylacetamide for acetic acid.

The secondary amines (II) are known or can be prepared by known methods and are also produced by adding corresponding secondary amines (III). If their solidification point is above the temperature used for extraction, it will be necessary to use a mixture of extracting agents (II) or to add a solvent, preferably an aromatic hydrocarbon such as p-diisopropylbenzene, such that no azeotrope is formed with the acid(s). This reduces the efficiency of the extracting agent (II), but there are still adequate advantages to be gained from this procedure in comparison with other methods, since the amount of solvent normally required to lower the solidification point is not great, being from 10% to 40% w/w of compound (II).

The molar amount of secondary amine (III) added is equal to the molar amount of secondary amine (II) consumed during extraction, although it can be increased beyond that amount if, for example, the secondary amine (II) is removed from the system by azeotropic distillation.

The amount of extracting agent (II) required depends on various factors, particularly the temperature, the amount and concentration of the acid, the number of separating stages, and other configurative factors influencing the establishment of equilibrium and, accordingly, the residence time required. No fundamental differences exist between the type of extracting agent used and the acid.

The extraction is preferably carried out at a temperature ranging from 0° to 70° C. The absorption capacity of the extracting agent with respect to the acid is greater in the lower part of this range, but the speed at which equilibrium is established is lower. The economically optimum temperature range is 20°–40° C.

When working at a temperature of from 20° to 40° C., from 1 to 10 kg of extracting agent (II) are required to extract 1 kg of acid during a residence time of from 1 to 5 minutes. This amount of extracting agent decreases with longer residence times and increases with shorter residence times. The said residence times apply to countercurrent extraction, the preferred method, carried out in a simple extraction column not equipped with any devices such as screens, trays, or packing material, and assuming that the extracting agent of lower density forms the continuous phase. The use of multi-stage extraction equipment, e.g. packed columns or tray towers preferably containing from 3 to 6 theoretical trays, effects an increase in efficiency, with the result that the amount of extracting agent used can be reduced according to known laws.

The above statements hold for an acid concentration of from 5% to 50% w/w of the aqueous solution, as is most commonly encountered in practice. The degree of enrichment is fairly constant at from 95% to 99% w/w; that is to say, when a 30% solution is processed the amount of acid remaining in the aqueous medium is from 0.1 to 0.3%, and if the extraction is carried out on a 10% solution the residual solution contains from 0.05 to 0.1% of acid. Generally, the most economical procedure is to carry out the extraction to the point where a mixture of extracting agent and 10–40% acid is obtained. This mixture is subjected to distillation to remove the water, after which the acid is distilled off in a second column. Alternatively, the system may be adjusted by known means so as to effect removal of only a portion of the water in the first column, whilst the remaining water is distilled off in the second column together with the acid. In this case, the product is not pure acid but a commercial concentrated acid.

The above explanations apply to the continuous production of carboxylic acid (I), which is virtually the only industrially significant method of preparation. Obviously, however, the process may be carried out batchwise, if desired, within the general framework of conditions stated above.

EXAMPLES

Example 1

A preheated feed comprising
91.5 g/h of formic acid
4.9 g/h of water
641.6 g/h of di-n-butylformamide
60.0 g/h of di-n-butylamine
and having a temperature of 90° C. was passed continuously to a glass column (diameter 28 mm, height 1,700 mm, glass ring packing) at a point approximately midway up the column (upper portion=700 mm, lower portion=1,000 mm), at a rate of 798.0 g/h. Distillation was carried out in vacuo (pressure at the head of the column=180 mbar). A mixture of formic acid (62.8 g/h) and water (13.1 g/h) is distilled off at the top of the column, where the temperature is 59° C., the reflux ratio being 0.5:1. The volume of the base of the column was adjusted so as to give a residence time of the bottoms of about 1 hour at a base temperature of 170° C. The bottoms were withdrawn continuously from the base of the column and comprised the following:
7.3 g/h of formic acid
713.3 g/h of di-n-butylformamide
1.5 g/h of di-n-butylammonium formate.

Mass measurements showed that 98% of the di-n-butylamine had been converted to di-n-butylformamide.

EXAMPLE 2

The experimental setup was as in Example 1. The pressure at the top of the column was reduced to 90 mbar, so that the temperature in the column was 42° C. at the top and 150° C. at the bottom. All other test conditions were as described in Example 1.

Mass measurements showed that 94% of the di-n-butylamine had been converted to di-n-butylformamide.

EXAMPLE 3

The experimental setup was as in Example 1. The pressure at the top of the column was raised to 350 mbar, so that the temperature in the column was 76° C. at the top and 190° C. at the bottom. All other test conditions were as described in Example 1.

Mass measurements showed that >99% of the di-n-butylamine had been converted.

EXAMPLE 4

The experimental setup was as in Example 1. The size of the base of the column was adjusted so as to give a residence time of the bottoms of 30 minutes at 170° C. All other test conditions were as described in Example 1.

Mass measurements showed that 96% of the di-n-butylamine had been converted to di-n-butylformamide.

EXAMPLE 5

The experimental setup was as in Example 1. The size of the base of the column was adjusted so as to give a residence time of the bottoms of 2 hours at 170° C. All other test conditions were as described in Example 1.

Mass measurements showed that >99% of the di-n-butylamine had been converted to di-n-butylformamide.

We claim:

1. A process for the isolation of a carboxylic acid of the general formula (I)

$$R^1\text{—COOH} \tag{I}$$

in which $R^1$ denotes hydrogen, methyl, ethyl, or vinyl, from a dilute aqueous solution thereof by extraction with a secondary amide of the general formula (II)

in which $R^1$ has the meanings stated, and $R^2$ and $R^3$ are independently of each other $C_1$–$C_8$-alkyl, $C_3$–$C_8$-cycloalkyl, $C_4$–$C_{20}$-cycloalkylalkyl, aryl, $C_7$–$C_{20}$-aralkyl, or $R^2$ and $R^3$ together form a 1,4- or 1,5-alkylene group which may be mono- to penta-substituted by $C_1$–$C_4$-alkyl, wherein the losses of secondary amide (II) are compensated by the addition of the corresponding amine of the general formula (III)

in which $R^2$ and $R^3$ have the meanings stated above which is converted to secondary amide (II) by reaction with carboxylic acid (I).

* * * * *

UNITED STATES PATENT AND TRADEMARK OFFICE
CERTIFICATE OF CORRECTION

PATENT NO. : 5,189,216

DATED : February 23, 1993

INVENTOR(S) : KIEFER et al.

It is certified that error appears in the above-identified patent and that said Letters Patent is hereby corrected as shown below:

ON THE COVER PAGE

Insert the following priority information on the cover page:

--[30]  Foreign Application Priority Data

July 23, 1990 [DE] Fed. Rep. of Germany ...... 4023353--.

Signed and Sealed this

Thirtieth Day of November, 1993

Attest:

BRUCE LEHMAN

*Attesting Officer*      *Commissioner of Patents and Trademarks*